(12) United States Patent
Nakano et al.

(10) Patent No.: US 8,994,753 B2
(45) Date of Patent: Mar. 31, 2015

(54) DISPLAYING EXTRACTED STRUCTURES FROM AN OCT IMAGE SUPERIMPOSED ON AN EYEGROUND IMAGE

(75) Inventors: Yuta Nakano, Tokyo (JP); Yasufumi Takama, Kawasaki (JP); Kenji Morita, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 696 days.

(21) Appl. No.: 13/217,754

(22) Filed: Aug. 25, 2011

(65) Prior Publication Data

US 2012/0050308 A1    Mar. 1, 2012

(30) Foreign Application Priority Data

Aug. 30, 2010 (JP) ................................. 2010-192385

(51) Int. Cl.
*G09G 5/00* (2006.01)
*A61B 3/00* (2006.01)
*G06T 5/50* (2006.01)

(52) U.S. Cl.
CPC ..... *A61B 3/0025* (2013.01); *G06T 2207/30041* (2013.01); *G06T 5/50* (2013.01); *G06T 2207/10101* (2013.01); *G06T 2207/20221* (2013.01)
USPC ........................................................ 345/637

(58) Field of Classification Search
CPC ...... G06F 17/24; G06K 9/00; G06K 9/00536; G05B 2219/23258
See application file for complete search history.

(56) References Cited

U.S. PATENT DOCUMENTS

| | | | |
|---|---|---|---|
| 7,593,559 B2 * | 9/2009 | Toth et al. | 382/128 |
| 7,794,083 B2 | 9/2010 | Tsukada | |
| 2008/0100612 A1 * | 5/2008 | Dastmalchi et al. | 345/418 |
| 2010/0189334 A1 | 7/2010 | Tomidokoro | |

FOREIGN PATENT DOCUMENTS

| | | | |
|---|---|---|---|
| JP | 2004-089224 A | 3/2004 |
| JP | 2007-325831 A | 12/2007 |
| JP | 2007-330558 A | 12/2007 |
| JP | 2010-142498 A | 7/2010 |

\* cited by examiner

*Primary Examiner* — Edward Martello
(74) *Attorney, Agent, or Firm* — Canon U.S.A., Inc. IP Division

(57) ABSTRACT

An image processing apparatus includes an extraction unit configured to extract a structure of a tested eye from an OCT image obtained by optical coherence tomography, an extraction unit configured to extract a structure of the tested eye from an eyeground image obtained by a scanning laser ophthalmoscope or a fundus camera, a calculation unit configured to calculate a reliability degree of the extraction for each of the extracted structures, and a display control unit configured to display the extracted structures superimposed on a image of eyeground according to the calculated reliability.

14 Claims, 14 Drawing Sheets

US 8,994,753 B2

DISPLAYING EXTRACTED STRUCTURES FROM AN OCT IMAGE SUPERIMPOSED ON AN EYEGROUND IMAGE

BACKGROUND OF THE INVENTION

1. Field of the Invention

The present invention relates to an image processing apparatus that displays an image of a photographing target, an image processing method, an image processing system, and a computer readable program storing memory.

2. Description of the Related Art

In the medical field, the image diagnosis is widely performed to detect a lesioned part or check the condition of a disease based on a captured image of a tested object.

The image diagnosis is employable to perform a detailed analysis based on comparison between images obtained by a plurality of different imaging apparatuses. For example, an eye doctor performs diagnosis based on an image obtained by an imaging apparatus, such as a fundus camera, a scanning laser ophthalmoscope (SLO), or an optical coherence tomography (OCT).

In general, the fundus camera can obtain a color image of an eyeground surface. The scanning laser ophthalmoscope can obtain a high-resolution image of an eyeground surface and an internal retina structure. The optical coherence tomography can obtain a retinal tomography image. Using a plurality of types of images obtainable from these imaging apparatuses enables a user to perform a detailed and accurate diagnosis on a surface of an eyeground and an internal structure thereof.

As an example technique capable of assisting such a medical diagnosis, a conventional technique discussed in U.S. Pat. No. 7,794,083 can display a projection image of a group of tomography images captured by the OCT in such a way as to be superimposed on an eyeground image. Further, the conventional technique discussed in U.S. Pat. No. 7,794,083 is capable of displaying structure information, such as a blood vessel area extracted from an OCT image, superimposed on an eyeground image.

Further, a conventional technique discussed in US2010/0189334 is capable of displaying a blood vessel extracted from an OCT image and a blood vessel extracted from an eyeground image.

However, a structure obtained from an OCT image and a structure obtained from an eyeground image (or an SLO image) are generally different from each other in extraction accuracy. Therefore, it is unable to indicate extraction reliability to a user by simply displaying an extracted structure.

SUMMARY OF THE INVENTION

According to an aspect of the present invention, an image processing apparatus includes an extraction unit configured to extract a structure of a tested eye from an OCT image obtained by optical coherence tomography, and configured to extract a structure of the tested eye from an eyeground image obtained by a scanning laser ophthalmoscope or a fundus camera; a calculation unit configured to calculate a reliability degree of the extraction for each of the extracted structures; and a display control unit configured to display the extracted structures superimposed on an image of eyeground according to the calculated reliability.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Figure 1:
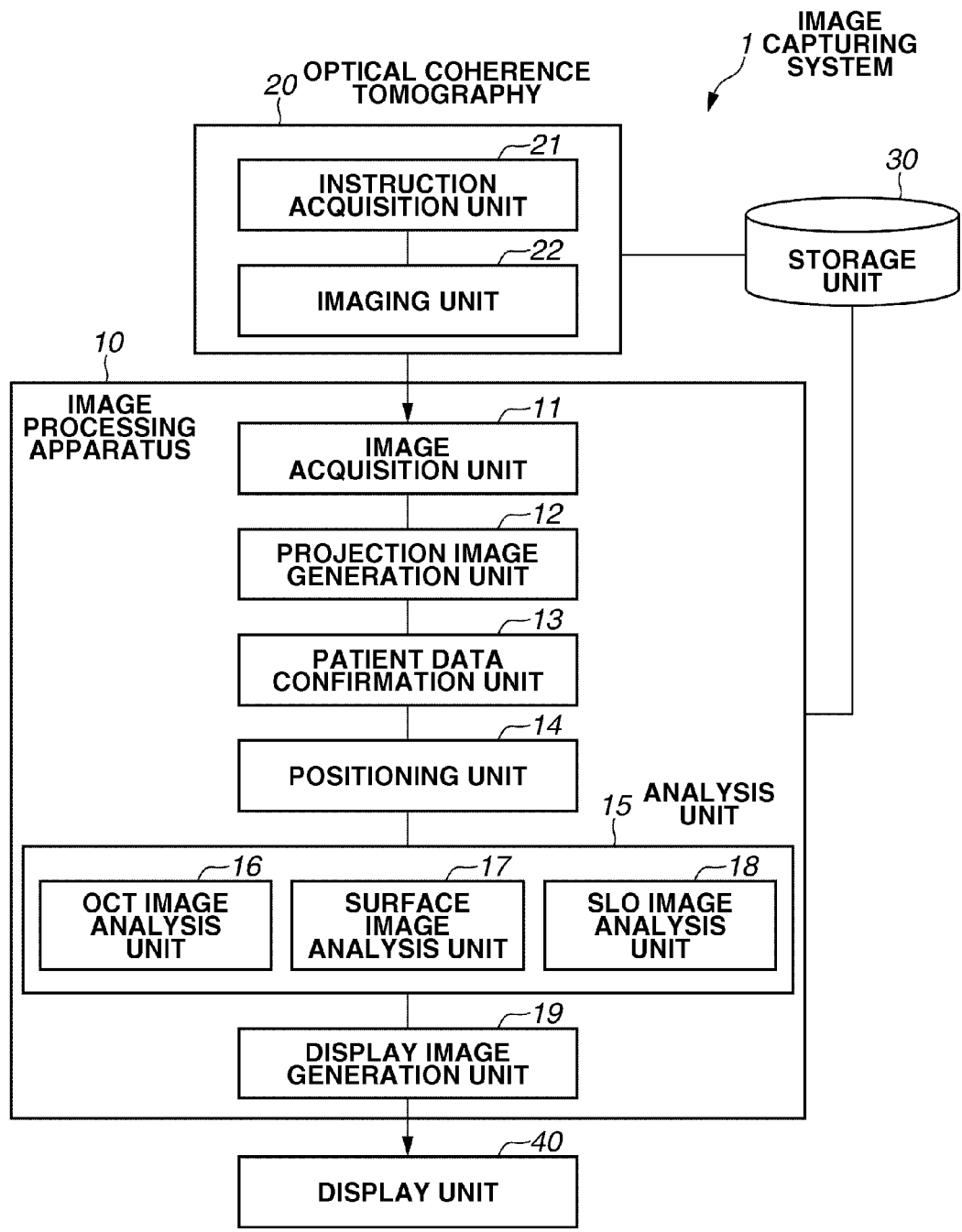
FIG. 1 illustrates a configuration of an image capturing system according to an exemplary embodiment of the present invention.

Various exemplary embodiments, features, and aspects of the invention will be described in detail below with reference to the drawings.

An example configuration of an image capturing system 1 according to the first exemplary embodiment is described below with reference to FIG. 1. The image capturing system 1 includes an image processing apparatus 10, an optical coherence tomography 20, a storage unit 30, and a display unit 40. The optical coherence tomography 20 can obtain a tomography image of a tested eye. The image processing apparatus 10 can extract a structure of a blood vessel based on the tomography image and a surface image of an eyeground captured by a fundus camera or an SLO image captured by a scanning laser ophthalmoscope.

Hereinafter, the surface image and the SLO image are collectively referred to as eyeground images. The display unit 40 can display a composite image including an extraction result superimposed on a corresponding image. The storage unit 30 stores tomography images captured by the optical coherence tomography 20 and images captured by the fundus camera.

The image processing apparatus 10 is connected to the optical coherence tomography 20, the storage unit 30, and the display unit 40 to communicate with each other. The image processing apparatus 10 includes various functional blocks illustrated in FIG. 1, as an appropriate hardware (e.g., ASIC or FPGA). The image processing apparatus 10 is configured to execute processing of the flowchart illustrated in FIG. 4.

More specifically, the image processing apparatus 10 includes an image acquisition unit 11, a projection image generation unit 12, a patient data confirmation unit 13, an alignment unit 14, an analysis unit 15, and a display image generation unit 19.

The image acquisition unit 11 can acquire a tomography image from the optical coherence tomography 20. The projection image generation unit 12 can generate a projection image projected on a plane perpendicular to the depth direction based on the tomography image acquired by the image acquisition unit 11.

The patient data confirmation unit 13 can search for an image relating to the same tested eye as the captured tomography image and extract, from the storage unit 30, any related image if it has been captured within a predetermined period of time before the shooting data and time of the tomography image. In the present exemplary embodiment, the patient data confirmation unit 13 searches for an eyeground surface image captured by the fundus camera or an SLO image captured by the scanning laser ophthalmoscope (SLO).

The alignment unit 14 can perform alignment for the tomography image and the surface image or the SLO image.

The analysis unit 15 can extract an organization structure, such as a blood vessel, from the tomography image and the surface image or the SLO image. The analysis unit 15 includes an OCT image analysis unit 16, a surface image analysis unit 17, and an SLO image analysis unit 18. The OCT image analysis unit 16 can analyze a tomography image. The surface image analysis unit 17 can analyze a surface image obtained by the fundus camera. The SLO image analysis unit 18 can analyze an image obtained by the SLO.

The display image generation unit 19 superimposes the extraction result on the eyeground image to generate superimposed image data for the display. In the present exemplary embodiment, the display image generation unit 19 is functionally operable as a display control unit configured to control the display unit 40. The display image generation unit 19 causes the display unit 40 to perform a display operation based on the generated image data.

Figure 2:
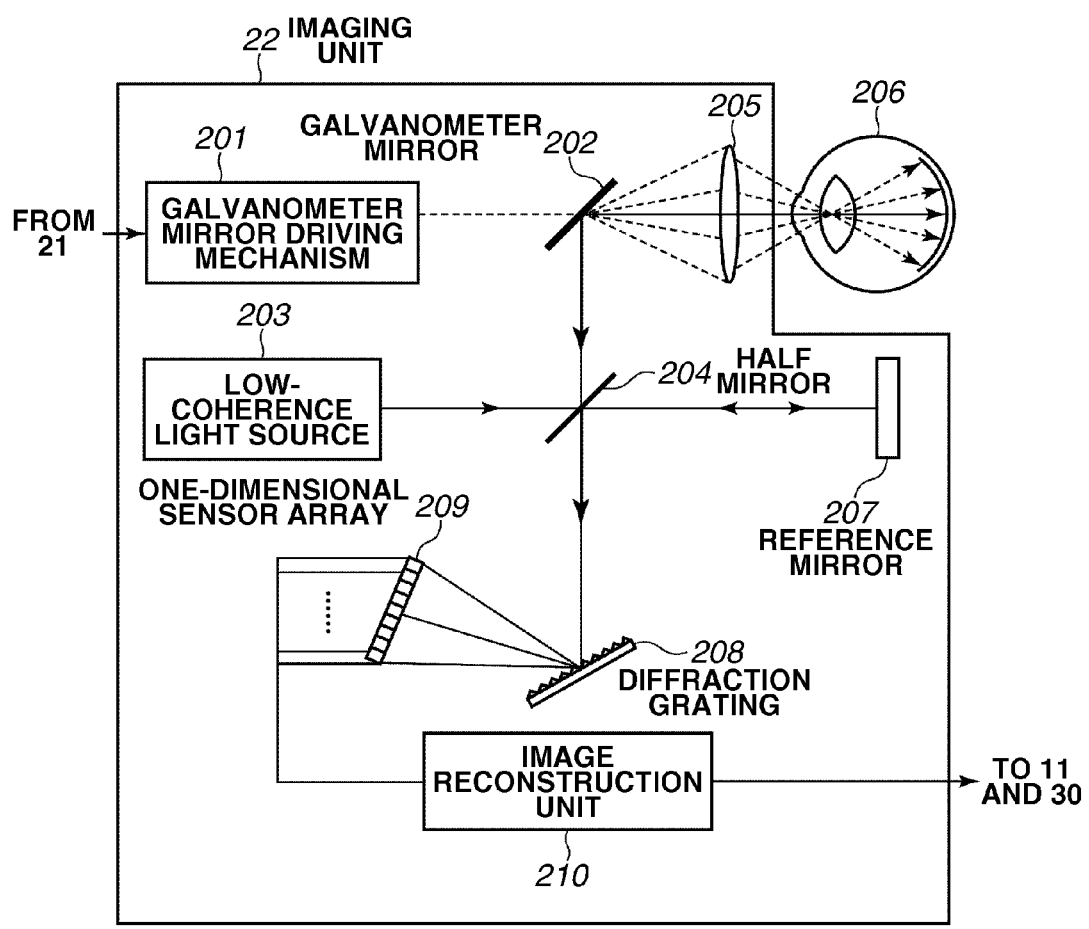
FIG. 2 illustrates a functional configuration of an imaging unit of the image capturing system according to an exemplary embodiment of the present invention.

Next, an example configuration of the optical coherence tomography 20 that can form a tomography image is described below with reference to FIG. 2. In the present exemplary embodiment, the optical coherence tomography 20 is an imaging apparatus that is operable according to the optical coherence tomography (OCT) principles. The optical coherence tomography 20 includes an instruction acquisition unit 21 and an imaging unit 22.

The instruction acquisition unit 21 acquires instruction information, which is provided to adjust the two-dimensional measurement range and the measurement depth for an eyeground surface of a tested eye. The imaging unit 22 includes a galvanometer mirror driving mechanism 201, a galvanometer mirror 202, a low-coherence light source 203, a half mirror 204, an objective lens 205, a reference mirror 207, a diffraction grating 208, a one-dimensional optical sensor array 209, and an image reconstruction unit 210.

The galvanometer mirror driving mechanism 201 drives the galvanometer mirror 202 based on the instruction information obtained from the instruction acquisition unit 21.

The low-coherence light source 203 can emit low-coherence light. The half mirror 204 separates the light from the low-coherence light source 203 into signal light and reference light. The signal light reaches a tested eye 206 via the galvanometer mirror 202 and the objective lens 205, and is reflected or scattered by the tested eye 206. The reference light travels toward the fixed reference mirror 207 and is reflected or scattered by the reference mirror 207. The half mirror 204 mixes the signal light returned from the tested eye 206 with the reference light returned from the reference mirror 207 to generate coherent light.

The diffraction grating 208 separates the coherent light into a plurality of wavelength components of wavelengths $\lambda 1$ to $\lambda n$. The one-dimensional optical sensor array 209 detects each wavelength component. The image reconstruction unit 210 reconstructs a retinal tomography image based on a detection signal including respective wavelength components of the coherent light output from the one-dimensional optical sensor array 209.

In the present exemplary embodiment, generating a one-dimensional image with signal light irradiated to an arbitrary position on an eyeground is referred to as "A scan." The one-dimensional image in the depth direction is referred to as "A scanned image." Further, scanning the eyeground with the signal light intermittently irradiated to the eyeground along an arbitrary line using the galvanometer mirror 202 is referred to as "B scan." The tomography image obtained by the B scan is referred to as "B scanned image."

Further, an image intersectional to the A scan direction, obtained from images obtained by performing the A scan at a plurality of positions within a predetermined area of the eyeground surface, is referred to as "C scanned image."

As described above, the optical coherence tomography 20 is an apparatus that can adequately perform a three-dimensional scanning operation on a retina of a tested eye to obtain an image of a retinal layer structure. Therefore, it is easy to extract a structure of a retinal deep part based on the tomography image of the OCT.

To the contrary, the fundus camera is configured to irradiate an eyeground with visible light and obtain a surface image of the eyeground based on reflected light. As the fundus camera uses the visible light, the fundus camera can acquire not only luminance information but also color information. Therefore, it is easy to extract a structure that appears on the eyeground surface.

Further, the scanning laser ophthalmoscope (SLO) is configured to perform a two-dimensional scanning operation while irradiating a predetermined portion of a tested eye with a weak laser beam to detect reflected light and form an image based on the detected light. In particular, if the SLO employs a confocal optical system, the SLO can perform simultaneous scanning (i.e., duplex scanning) with incident light and reflected light to detect reflected light via a confocal aperture (such as a pinhole).

Thus, the SLO can reduce adverse influences that may be caused by unnecessary scattered light. As a result, the SLO can greatly improve the contrast of an image. The SLO can improve the three-dimensional spatial resolution. The SLO has the capability of obtaining a surface image, and is further capable of expressing an internal structure of the retina as an image. Therefore, the SLO can extract surface information and internal structure information.

The storage unit 30 stores surface images and SLO images that correspond to the tomography images obtained from the OCT. Analyzing a plurality of images, which are mutually different in characteristics, enables to extract a different structure. Further, it becomes feasible to confirm extraction reliability.

Figure 3:
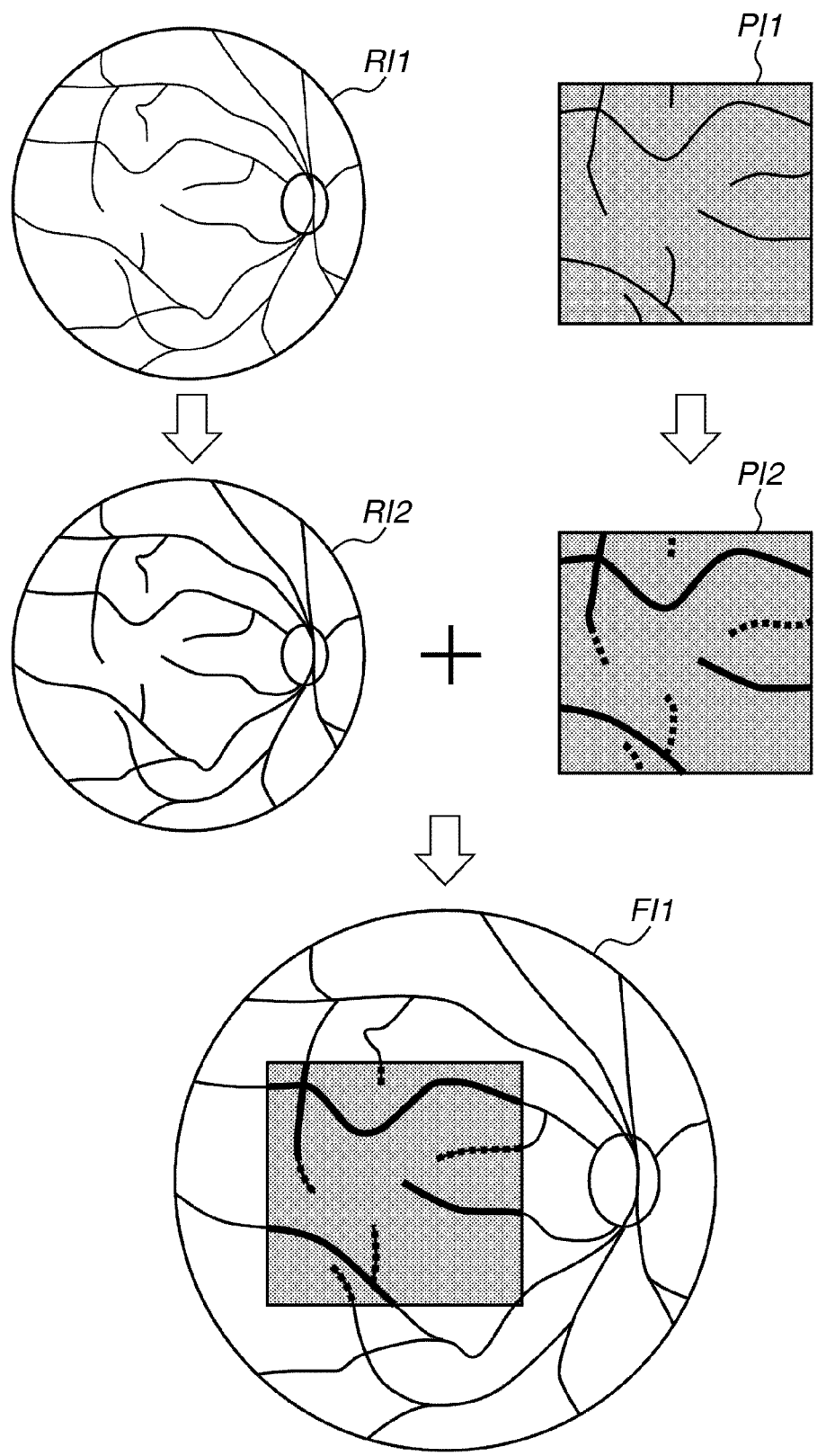
FIG. 3 schematically illustrates example processing that can be performed by an image processing apparatus according to an exemplary embodiment of the present invention.

The above-described features of the present exemplary embodiment are described in detail below with reference to FIG. 3. FIG. 3 illustrates a surface image RI1 of an eyeground obtained by the fundus camera and a projection image PI1 generated based on a tomography image obtained by the OCT. The image processing apparatus 10 extracts a blood vessel area from the surface image RI1 and the tomography image or the projection image (hereinafter, referred to as "OCT image"). FIG. 3 further illustrates two images RI2 and PI2 each including a blood vessel extraction result superimposed on the eyeground image and the projection image, respectively. A bold line indicates the extracted blood vessel area.

Then, the image processing apparatus 10 forms a composite image FI1 that combines the eyeground image and the projection image and displays the composite image FI1 together with the blood vessel areas extracted from respective images on the display unit 40. Through the above-described processing, the surface image of the eyeground, the accumulated image, and the structure information extracted from respective images can be confirmed on a single image.

Further, it is easy to extract a relatively thick blood vessel from the eyeground image RI2. However, if the contrast between the blood vessel and the retina is low, it may be difficult to extract the blood vessel area. On the other hand, each blood vessel can be extracted from the projection image PI2 regardless of the thickness of the blood vessel. Further, it is feasible to extract a structure that cannot be extracted from the surface image (e.g., choroidal neovascularization).

However, due to noise or insufficient resolution, a terminal end portion BP2 of the blood vessel tends to be extracted as a discontinuous part. As described above, displaying the integrated structure information extracted from the eyeground image and the OCT image having different characteristics enables to mutually complement information of respective images and provide a greater amount of information.

Further, reliability information with respect to extraction results can be obtained by confirming the extraction results from respective images. For example, when a blood vessel is extracted from the same area of the surface image and the tomography image, it can be determined that the reliability of the extracted blood vessel is higher.

Next, an example flow of the above-described display processing that can be executed by the image processing apparatus 10 is described with reference to FIG. 4.

Figure 5:
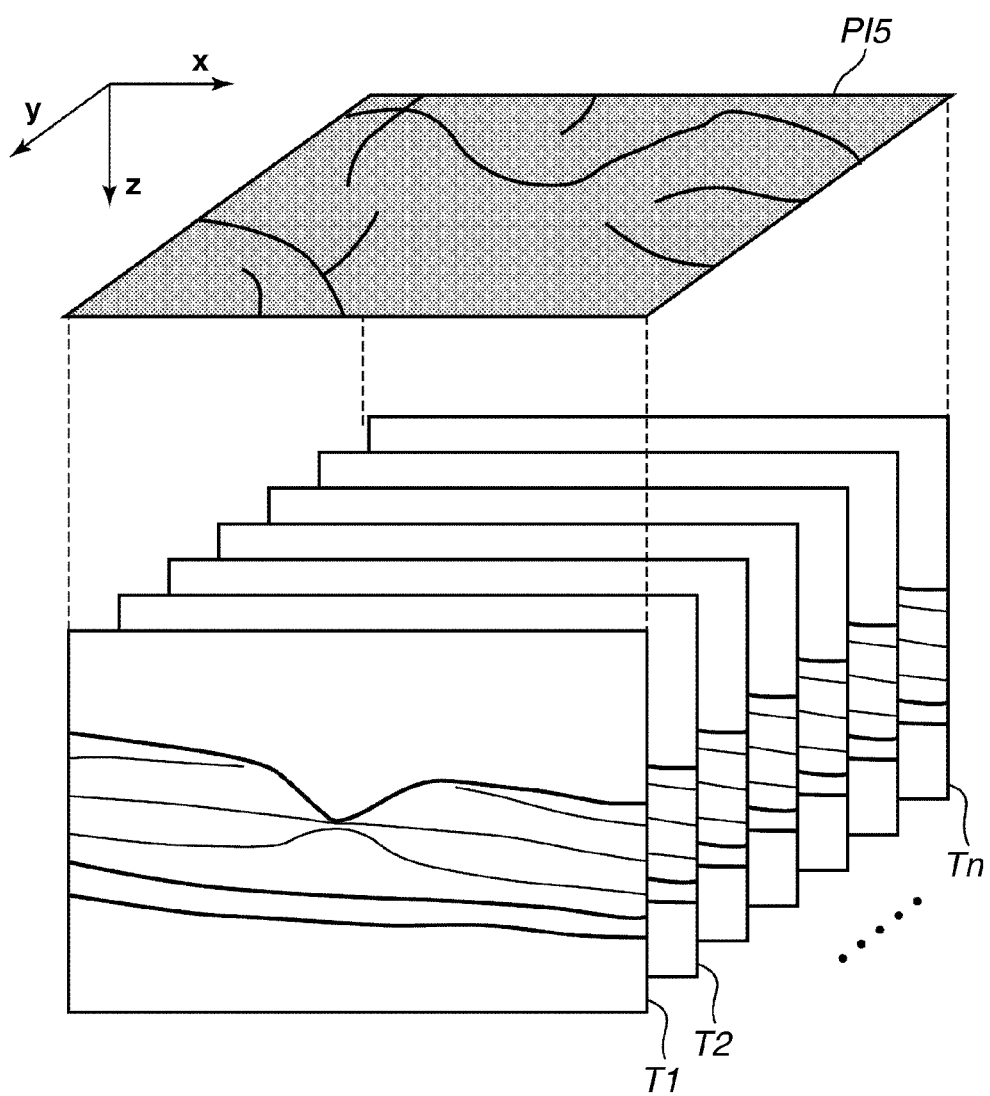
FIG. 5 illustrates an OCT image group and a projection image.

In step S401, the image acquisition unit 11 acquires tomography images from the optical coherence tomography 20. In the present exemplary embodiment, the tomography image acquired in step S401 is a tomography image group including a plurality of B scanned images as illustrated in FIG. 5. Further, the image acquisition unit 11 acquires another image of the same tested eye corresponding to the tomography image group from the storage unit 30.

For example, as another image, the image acquisition unit 11 acquires an eyeground surface image captured by the fundus camera or an SLO image captured by the scanning laser ophthalmoscope (SLO). In the present exemplary embodiment, the image processing apparatus 10 performs the following processing to acquire the surface image.

In step S402, the projection image generation unit 12 generates a projection image based on the tomography image group. As illustrated in FIG. 5, a summed-up value of luminance values at each pixel of tomography images T1 to Tn, simply added along the positive direction of the z axis, is equal to a pixel value of a projection image PI5.

According to another example, a value obtained by dividing the sum of luminance values by the number of added pixels is equal to the pixel value of the projection image PI5. Further, according to another example, a maximum luminance value or a minimum luminance value at each position in the depth direction is equal to the pixel value of the projection image PI5. Further, according to another example, a pixel value calculated in an arbitrary range of the z-axis direction, or in a range corresponding to specific layers only, can be used.

Further, according to another example, a retinal layer area that extends along an inner limiting membrane (ILM) of the retina on one side and along the interface between inner and outer segments of the photoreceptors (IS/OS) on the other side is an area that can be used to generate a projection image. A maximum luminance value in the above-described area is equal to the pixel value of the projection image PI5.

A high luminance area existing in a region between the ILM and the IS/OS is relatively small. A lesioned part, such as a leucoma, can be imaged as a high luminance area. Therefore, such a lesioned part can be displayed on the projection image in such a way as to let a user confirm a lesioned part area easily.

In step S403, the alignment unit 14 performs alignment for the projection image and the eyeground image. In the present exemplary embodiment, the alignment unit 14 obtains a scale (Sx, Sy), position coordinates (x, y), and a rotational (rot) component of the eyeground image relative to the coordinate system of the projection image. The alignment unit 14 adjusts the position of the projection image and the position of the eyeground image based on the obtained data.

Further, a mean square error of the luminance value in the entire region of the projection image and the eyeground image is usable to calculate an index that can check the matching between images. More specifically, a parameter that can minimize the mean square error can be obtained as a result of the present processing step.

The index for the alignment is not limited to the above-described example. The mean square error of the luminance value can be replaced by a correlation coefficient or a mutual information mount. If the alignment unit 14 uses structure information extracted in step S405 in the alignment for the projection image and the eyeground image as described below, the alignment unit 14 can more accurately perform the alignment.

In step S405, the analysis unit 15 extracts an organization structure, such as a blood vessel, an optic disc portion, or a macula portion, from the eyeground image. In the eyeground image, the blood vessel appears as a thin linear structure. Hence, the analysis unit 15 uses a filter capable of enhancing a linear structure to extract such a thin blood vessel.

In the present exemplary embodiment, the filter used by the analysis unit 15 is a line segment enhancing filter, which is based on the contrast and, in a case where the line segment is the structure element, is configured to calculate a difference between an average luminance value in a structure element and an average value in a local area surrounding the structure element.

In the present exemplary embodiment, a multi-value area obtained as a filter processing result can be directly used as a blood vessel extraction result. Alternatively, an area binarized using a predetermined threshold value can be used as an extraction result. However, the linear structure enhancing method is not limited to the above-described example. For example, an appropriate differential filter (e.g., a Sobel filter or a Laplacian filter) can be used.

Further, the analysis unit 15 can calculate eigenvalues of Hessian matrix for each pixel and extract an area similar to a line segment based on a combination of two eigenvalues obtained as a calculation result. Further, the analysis unit 15 can use any conventionally-known blood vessel extraction method, such as top-hat calculation that simply regards a line segment as a structure element. Further, the analysis unit 15 can extract an optic disc portion and a macula portion based on luminance value information of the image.

Further, the analysis unit 15 extracts a leucoma portion as a lesioned part. The leucoma area is locally present in an eyeground image and has a higher luminance value compared to its peripheral portion. Therefore, the analysis unit 15 detects the leucoma area by performing the top-hat calculation and threshold value processing. The analysis unit 15 can use anatomical features to extract a drusen or bleeding. An anatomical feature of the drusen, which is detectable from an eyeground image, is a whitish lump.

A bleeding area has a luminance value that is lower than that of a non-bleeding area in each of RGB components. If the amount of bleeding is large, the luminance value at the bleeding portion is considerably lower than that of a blood vessel portion. Therefore, the analysis unit 15 performs extraction processing considering the above-described characteristic features.

In step S406, the analysis unit 15 extracts a blood vessel, an optic disc portion, a macula portion, and a lesioned part from the OCT image. If a blood vessel is present in the OCT image, a pseudo image may be generated because the signal attenuates if the position is deeper than the blood vessel (i.e., an absorption material). The analysis unit 15 can detect the blood vessel considering the above-described features.

More specifically, the analysis unit 15 uses the Sobel filter that can enhance the contrast from a pixel having a lower luminance value to a pixel having a higher luminance value when seen from the depth direction of the A-scan. The analysis unit 15 obtains a converted image as a Sobel image. In this manner, when the Sobel filter having adequate directivity is used, the inner limiting membrane (ILM) L1 of the retina and the interface between inner and outer segments of the photoreceptors (IS/OS) L2 can be enhanced as illustrated in FIG. 6.

Next, the analysis unit 15 generates a profile of the luminance value in each A-scan of the Sobel image and counts the number of peak points. FIG. 6 illustrates a profile PS1 of the Sobel image at an A-scan position A1 where no blood vessel is present and a profile PS2 of the Sobel image at an A-scan position A2 where a blood vessel is present. The analysis unit 15 counts the number of peak points of each profile that is equal to or greater than a threshold value Th along the depth direction.

Figure 6:
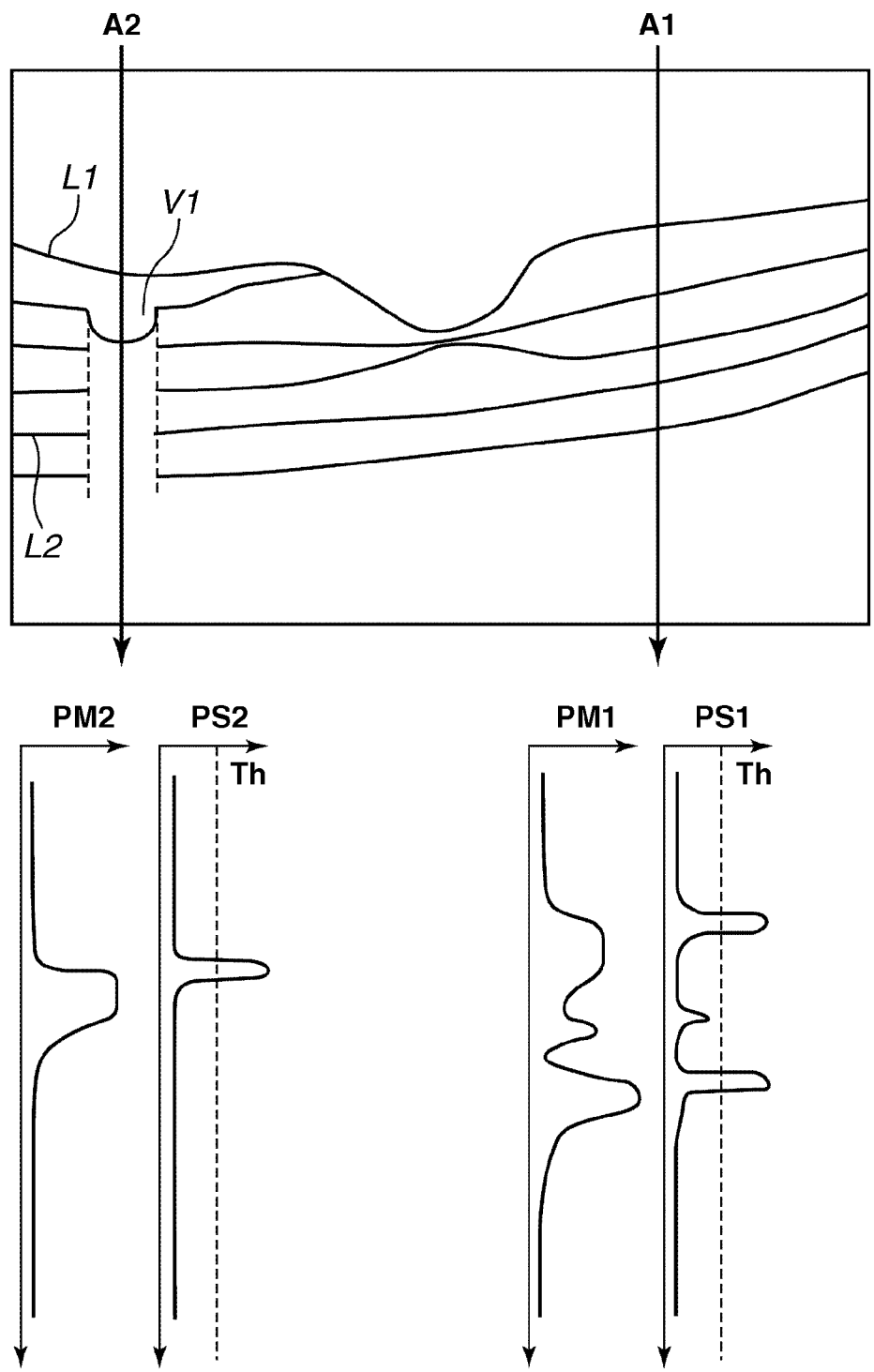
FIG. 6 illustrates an OCT image and A-scan profiles.

As understood from the profile PS1 illustrated in FIG. 6, if the retinal layer structure is normal, there are two peak points that are equal to or greater than the threshold value Th. On the other hand, as understood from the profile PS2 illustrated in FIG. 6, if only one or no peak point is present, it is determined that a blood vessel is present at the A-scan position A2. The analysis unit 15 performs the above-described processing for all A-scans to extract a blood vessel structure.

As another example of the blood vessel extraction method, the analysis unit 15 can extract a blood vessel from the projection image. Due to the influence of a pseudo image, a blood vessel appears on the projection image as a linear structure having a lower luminance value compared to its peripheral portion. Hence, the analysis unit 15 uses the filter employed in the processing of step S405 that can enhance a linear structure to extract a blood vessel structure.

The analysis unit 15 can extract an optic disc portion by checking the presence of a retinal pigment epithelium layer because the retinal pigment epithelium layer is not present at the optic disc portion. The analysis unit 15 can extract a macula portion by checking the presence of a nerve fiber layer (NFL) because the nerve fiber layer is not present at the macula portion.

Further, the analysis unit 15 extracts a choroidal neovascularization and a leucoma as lesioned parts. If a choroidal neovascularization is present, a higher luminance area appears in a region deeper than the interface between inner and outer segments of the photoreceptors on the OCT image. Considering the above-described features, the analysis unit 15 adds up luminance values in the region deeper than the interface between inner and outer segments of the photoreceptors in each A-scan.

If the added-up luminance value is equal to or greater than a threshold value, the analysis unit 15 determines that a choroidal neovascularization is present and extracts the choroidal neovascularization. The analysis unit 15 can extract a leucoma by detecting an area having a higher luminance value than a predetermined threshold value in a region between the ILM and the IS/OS.

As another example, as an example extraction of the organization structure in steps S405 and S406, the analysis unit 15 can extract different organization structures from respective images. The organization structure to be extracted from each image is selectable considering the extraction accuracy. For example, the organization structures extractable from the surface image obtained by the fundus camera include a blood vessel, a leucoma, a "disc" area of the optic disc portion, and a macula portion.

The organization structures extractable from the OCT image include a choroidal neovascularization and a "cup" area of the optic disc portion. Structures extractable based on characteristic features of respective images can be clearly shown by displaying the extracted organization structures.

In step S407, the display image generation unit 19 generates a superimposed image to be displayed on a screen. In the present exemplary embodiment, the display image generation unit 19 sets a predetermined transparency to the projection image and superimposes the transparent projection image on the surface image. For example, alpha blending processing is usable for the setting of the transparency.

An example "value" of a pixel to be displayed can be determined according to the following formula (1), in which img1 represents a pixel value of the surface image, img2 represents a pixel value of the superimposed projection image, and α is a value relating to the transparency.

$$\text{value} = \text{img1} \times (1.0 - \alpha) + \text{img2} \times \alpha \tag{1}$$

According to the above-described formula (1), when the value α is small, the transparency is high. When the value α is large, the transparency is low. In other words, the value (1−α) indicates the transparency.

In step S408, the display image generation unit 19, which is functionally operable as the display control unit, causes the display unit 40 to display the image formed in step S407.

Figure 7:
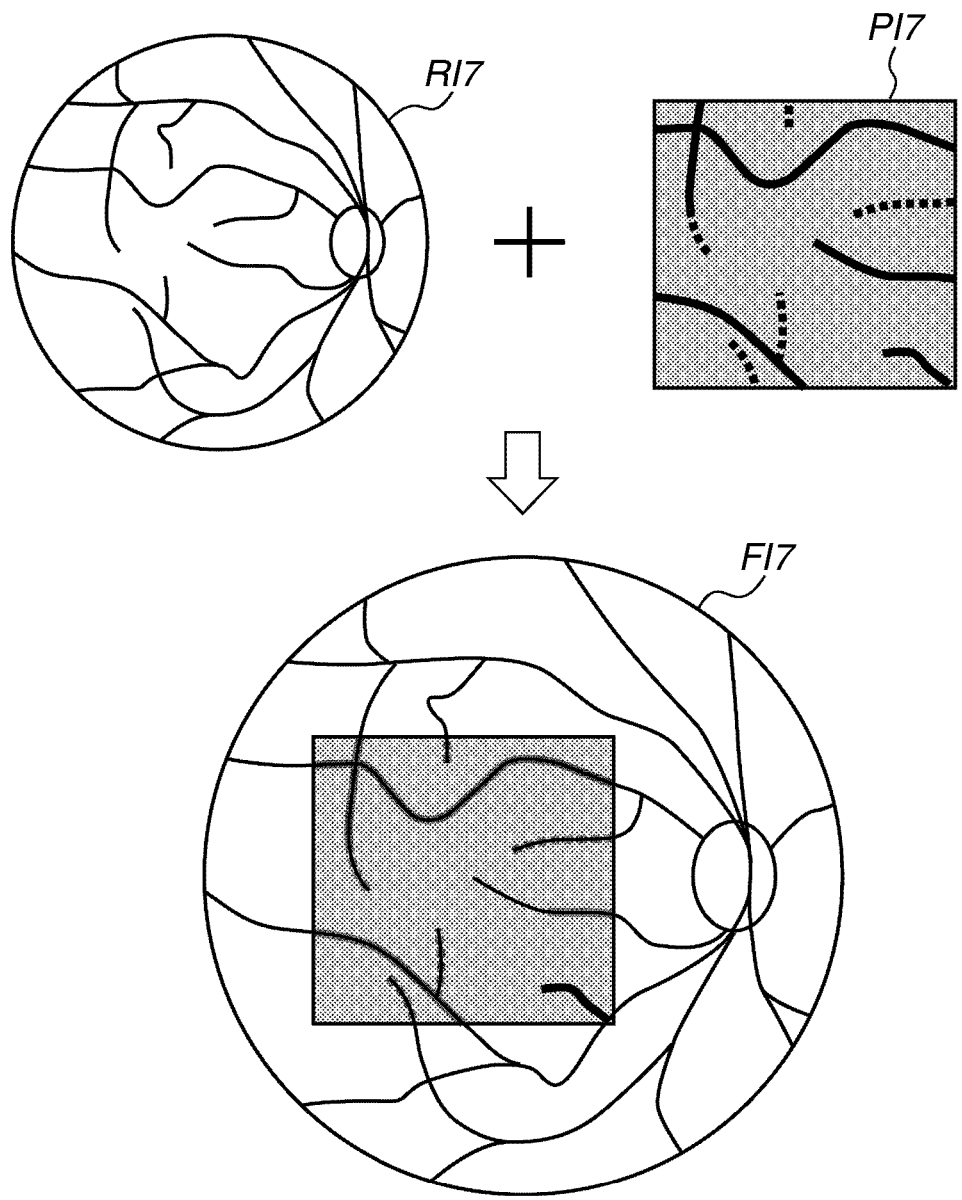
FIG. 7 illustrates an example of the display that can be displayed on a display unit.

FIG. 7 illustrates an example of the screen that can be displayed on the display unit 40 by the display control unit. According to the example of the display illustrated in FIG. 7, a projection image having a predetermined transparency is superimposed on a surface image.

The display control unit forms an image in such a way as to superimpose a structure extracted from the OCT image on the projection image and a blood vessel area extracted from the surface image on the surface image. The display control unit can add color to a specific structure (e.g., a blood vessel or a lesioned part) on the image.

As described above, an image acquired from the fundus camera is different from a tomography image acquired from the OCT in characteristics. Users can easily confirm structures extracted from these different images on a single image. Therefore, physicians can improve their diagnosis efficiency.

In particular, the displayed projection image has an appropriate transparency. Therefore, color information of the eyeground surface, the structure extracted from the projection image, and the structure extracted from the surface image are simultaneously displayed in an area where the projection image is superimposed on the surface image.

Thus, plenty of information can be provided to each user. Further, diagnosticians can confirm a plurality of different features about each tested eye on a single eyeground image. As a result, their diagnosis efficiency can be improved.

As another example of the display, it is useful to differentiate the color added to a blood vessel area in the OCT image from the color added to a blood vessel area in the eyeground image. In this case, users can check the color of each blood vessel if it is necessary to identify the source from which the blood vessel is originated.

Further, as another method for letting users know the extraction source, it is useful to change a flickering pattern or change the type of a frame line surrounding an area. In particular, when the type of the frame line is changed according to the extraction source, users can discriminate each image of the extraction source and can easily confirm a pixel value of an extraction target area in the image.

Further, as another example of the display, it is useful to differentiate the color added to a blood vessel area extracted from both of the OCT image and the eyeground image, the color added to a blood vessel area extracted solely from the OCT image, and the color added to a blood vessel area extracted solely from the eyeground image, from each other. Users can easily recognize the extraction source of each blood vessel based on its color information.

Further, users can easily discriminate a blood vessel extracted from both images, a blood vessel extracted from the surface image acquired from the fundus camera, and a blood vessel extracted from the tomography image acquired from the OCT. The blood vessel area extracted from both images is more reliable. Thus, the extraction reliability can be improved.

As described above, when the structure information extracted from the OCT image and the eyeground image are simultaneously displayed, mutually complementing features of respective images becomes feasible. As a result, plenty of highly accurate information can be provided to each user.

In a second exemplary embodiment, example processing for changing the display pattern of a projection image according to a structure extraction result obtained by the analysis unit 15 is described below. When structure information is extracted from an image, the visibility of an extracted structure is variable depending on the type of a structure in each of the projection image and the eyeground image.

Hence, the present exemplary embodiment sets a lower transparency for a projection image of the display image in a case where confirming a target structure on the projection image is easier, and sets a higher transparency in a case where confirming a target structure on the eyeground image is easier.

A configuration of the apparatus according to the present exemplary embodiment is different from that of the first exemplary embodiment in that the transparency of the projection image is determined according to a structure extracted by the display image generation unit 19. Example processing that can be performed by the display image generation unit 19 is described below.

Figure 8:
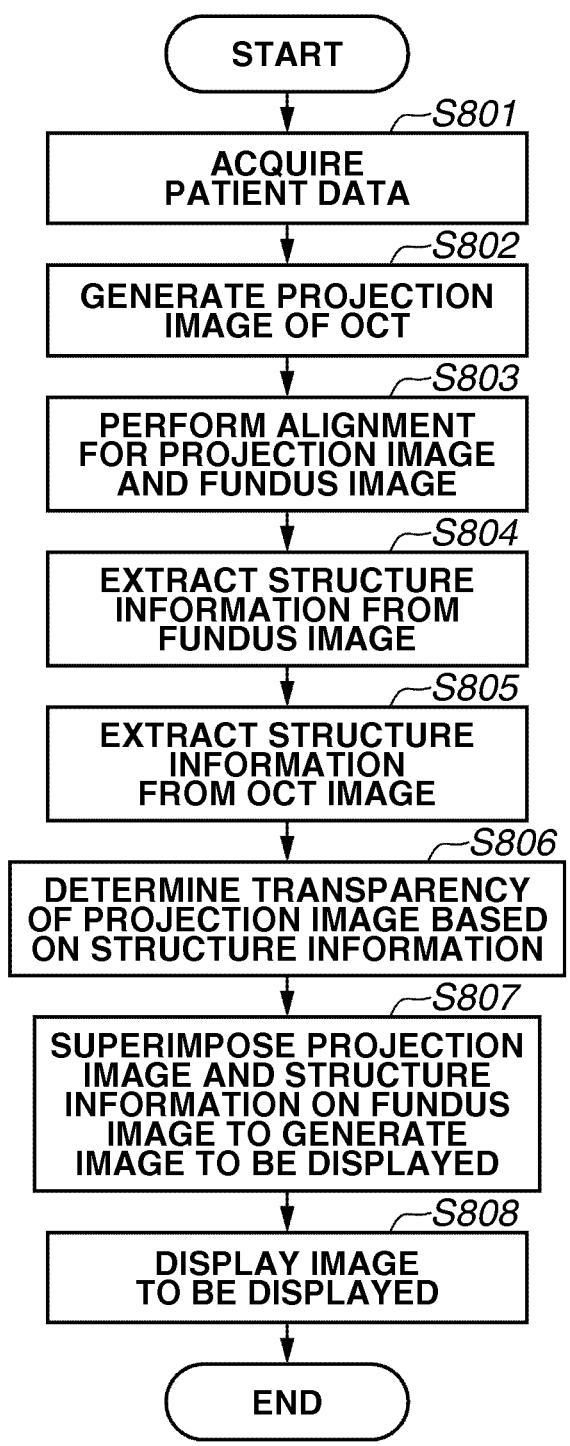
FIG. 8 is a flowchart illustrating an example procedure of another processing that can be performed by the image processing apparatus according to an exemplary embodiment of the present invention.

Example processing to be performed in step S807 according to the second exemplary embodiment is described in detail below with reference to FIG. 8. Processing to be executed in steps S801 to S805, S807, and S808 is similar to the processing performed in steps S401 to S407 of the flowchart illustrated in FIG. 4 described in the first exemplary embodiment and therefore the description thereof is not repeated.

In step S806, the display image generation unit 19 determines a transparency of the projection image according to an extraction result obtained by the analysis unit 15. In the present exemplary embodiment, the transparency is set to be an appropriate value in a range from 0% to 100%. When the numerical setting value is large, the transparency of a displayed image is high. In the present exemplary embodiment, if any structure information is extracted in step S804 and step S805, the display image generation unit 19 determines the transparency based on the extracted information.

Figure 9A:
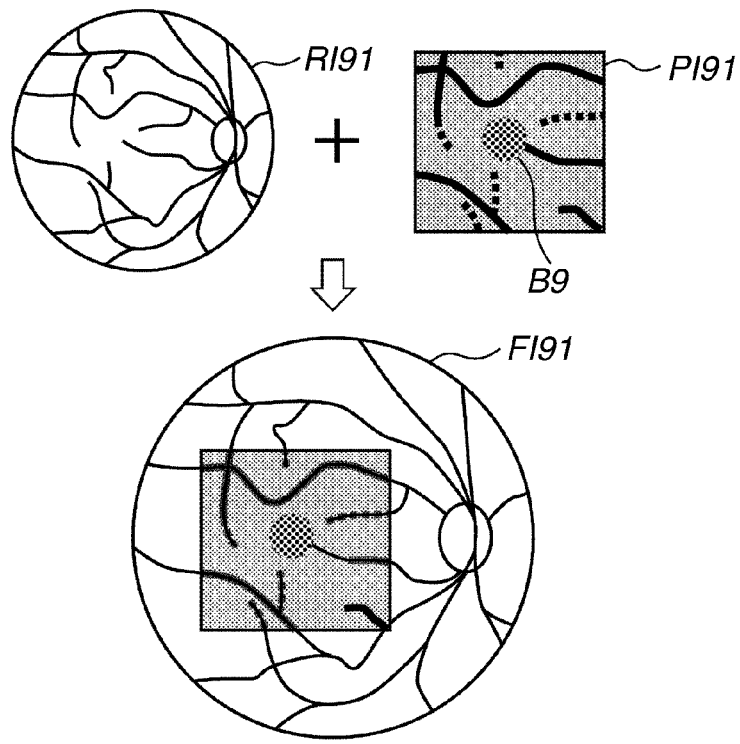
FIG. 9A and FIG. 9B illustrate examples of the display, in which the transparency is changed to display a projection image superimposed on a surface image.

FIG. 9A illustrates an example of the display in a case where a choroidal neovascularization B9 is extracted from an OCT image. The choroidal neovascularization is easily recognized as a lesioned part on a projection image PI91 rather than an eyeground image RI91. Therefore, the display image generation unit 19 sets 25% as the transparency for the projection image PI91.

Figure 9B:
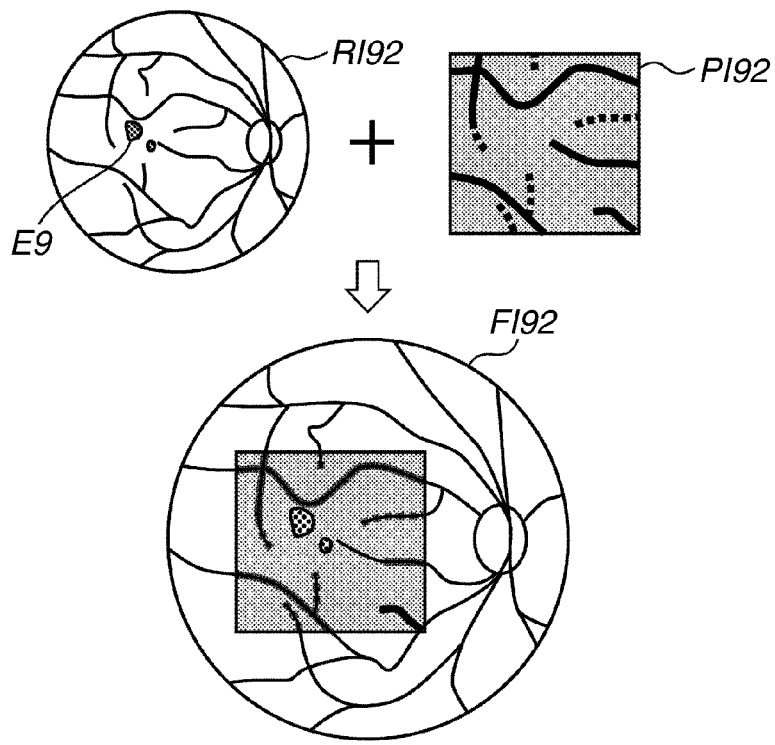

Further, as illustrated in FIG. 9B, if a leucoma E9 is extracted from an area where the projection image is superimposed, the leucoma is easily recognized as a lesioned part on an eyeground image RI92 rather than a projection image PI92. Therefore, the display image generation unit 19 sets 75% as the transparency for the projection image PI92.

Table information correlating the type of a lesioned part extracted from each image with transparency is stored in a memory unit (not illustrated). The display image generation unit 19 can appropriately set a transparency value with reference to the table information. If in step S808 the display image generation unit 19 performs formation of a display image based on the transparency having been set in step S806, composite (overlapped) images FI91 and FI92 can be obtained.

In a case where a leucoma is present, it is desired to confirm the state of the leucoma in relation to a corresponding surface image. Therefore, the display image generation unit 19 increases the transparency of the projection image to improve the visibility of the surface image for a user. Thus, a leucoma image easy to view can be provided to the user.

On the other hand, in a case where a choroidal neovascularization is present, it is desired to confirm the state of the lesioned part in relation to a corresponding tomography image (or projection image), i.e., the extraction source. Therefore, the display image generation unit 19 lowers the transparency of the projection image to improve the visibility of the lesioned part for a user.

Further, when a frame surrounding a specific area (e.g., an extracted blood vessel or a lesioned part) is displayed together with a target structure, the display image generation unit 19 lowers the transparency of the projection image in a region where the choroidal neovascularization is present so that the visibility of the choroidal neovascularization can be improved on the projection image.

Further, the display image generation unit 19 increases the transparency of the projection image in a region where the leucoma is present so that the visibility of the leucoma area can be improved on the surface image.

Another example setting of the transparency is described below. If a tested object is in an advanced stage of a disease, a plurality of types of lesioned parts may appear simultaneously. For example, it is assumed that a leucoma is extracted from a surface image and a choroidal neovascularization is extracted from a tomography image.

In this case, the display image generation unit 19 performs processing for changing the transparency of the projection image for each partial region. More specifically, the display image generation unit 19 lowers the transparency of the projection image in a partial region that involves or surrounds the choroidal neovascularization extracted position.

On the other hand, the display image generation unit 19 increases the transparency of the projection image in a partial region that involves or surrounds the leucoma extracted position. When the transparency is changed for each partial region as described above, each user can easily confirm a structure extracted from an image.

As another example processing for changing the display pattern, the display image generation unit 19 can increase or lower the luminance value instead of changing the transparency. When the transparency of a projection image to be superimposed is entirely or locally changed according to an image analysis result, an image that more clearly displays a lesioned part can be provided to each user.

In a third exemplary embodiment, after structure information is extracted from each of the eyeground image and the OCT image (see steps S403 and S404 in the first exemplary embodiment), the image processing apparatus 10 calculates a reliability degree of each extraction result and determines a display pattern with reference to the calculated reliability degree.

For example, when a blood vessel is extracted as structure information, the blood vessel may be extracted from both the eyeground image and the OCT image. In some cases, the blood vessel may be extracted solely from either one of the eyeground image and the OCT image. Hence, in the present exemplary embodiment, the image processing apparatus 10 calculates a reliability degree of each blood vessel extraction result from the eyeground image and the OCT image and determines whether to display each blood vessel extraction result on the image with reference to the calculated reliability degree.

A configuration of the apparatus according to the present exemplary embodiment is different from that of the first or second exemplary embodiment in that the analysis unit 15 calculates a reliability degree value that indicates the reliability of each extracted structure. Further, the configuration of the apparatus according to the present exemplary embodiment is different in that the display image generation unit 19 changes the display pattern of an image according to the calculated reliability degree. Example processing that can be performed by the analysis unit 15 and the display image generation unit 19 according to the present exemplary embodiment is described below.

Figure 10:
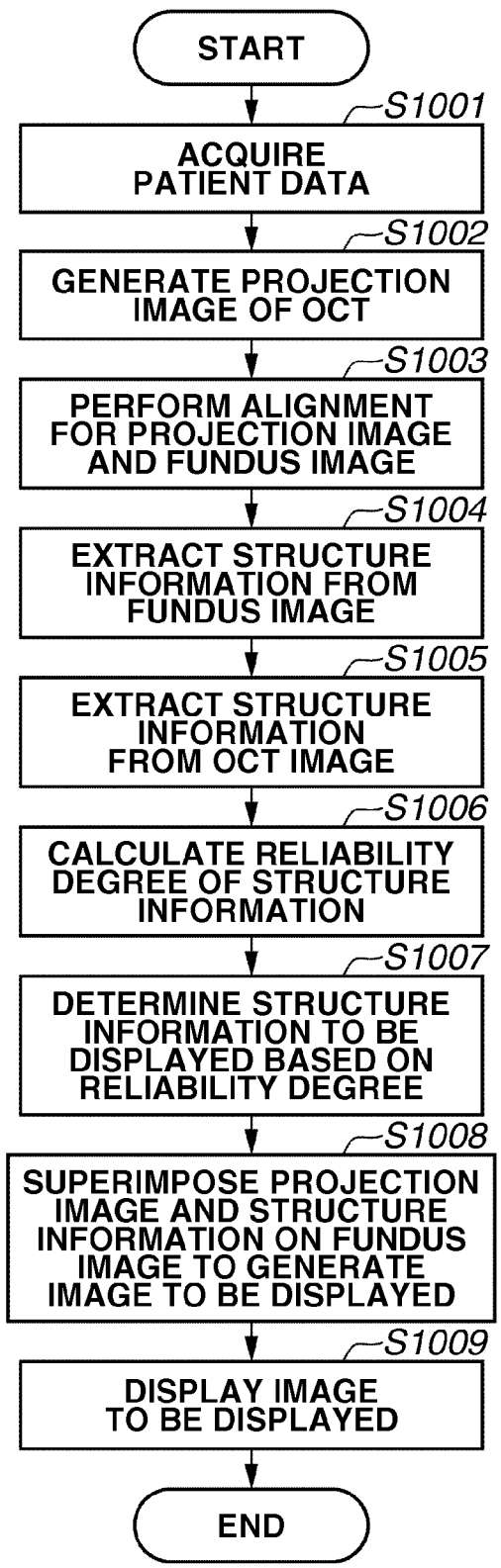
FIG. 10 is a flowchart illustrating an example procedure of another processing that can be performed by the image processing apparatus according to an exemplary embodiment of the present invention.

Hereinafter, processing to be performed in step S1006 and step S1007 according to the third exemplary embodiment is described in detail below with reference to FIG. 10. Processing to be executed in steps S1001 to S1005, S1008, and S1009 is similar to the processing performed in steps S401 to S407 of the flowchart illustrated in FIG. 4 described in the first exemplary embodiment and therefore the description thereof is not repeated.

In step S1006, the analysis unit 15 calculates a reliability degree of structure information with reference to the extraction results obtained by the OCT image analysis unit 16 and the surface image analysis unit 17. In the present exemplary embodiment, the analysis unit 15 calculates a reliability degree based on the blood vessel extraction results obtained in step S1004 and step S1005.

Figure 11A:
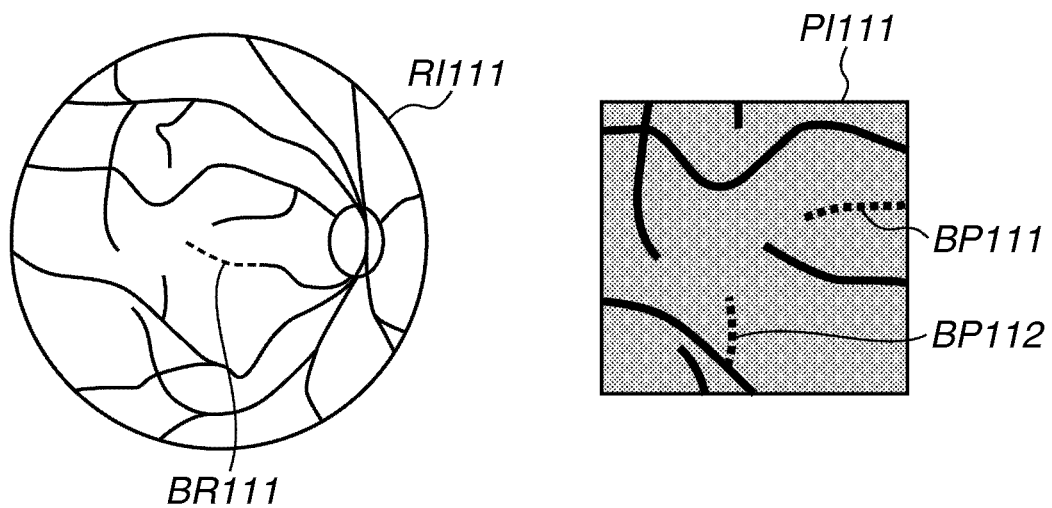
FIG. 11A illustrates blood vessel areas extracted from an eyeground image and an OCT image.

FIG. 11A illustrates a blood vessel extraction result RI111 extracted from an eyeground image and a blood vessel extraction result PI111 extracted from an OCT image and superimposed on a projection image. As understood from FIG. 11A, the extraction result RI111 includes a dotted line portion BR111 that cannot be identified as either a blood vessel or noise. The extraction result PI111 includes a dotted line portion BP111 that cannot be identified as either a blood vessel or noise. Further, a blood vessel BP112 was not extracted from the eyeground image and extracted only from the OCT projection image.

To calculate a reliability degree based on the above-described results, the analysis unit 15 checks if a neighboring pixel (i.e., a pixel positioned adjacent to a target pixel) includes a blood vessel in respective images. Then, if the target pixel is a blood vessel and the blood vessel is present in the neighboring pixel, the analysis unit 15 allocates a reliability degree "2."

Further, if the target pixel is a blood vessel and the blood vessel is not present in the neighboring pixel, and if the target pixel is not a blood vessel and the blood vessel is present in the neighboring pixel, the analysis unit 15 allocates a reliability degree "1." In other cases, the analysis unit 15 does not allocate any reliability degree. The analysis unit 15 repetitively performs the above-described processing for each of the eyeground image and the projection image.

Further, the calculation with respect to reliability degree is not limited to the blood vessel. The analysis unit 15 can calculate a reliability degree for each lesioned part extracted in steps S1004 and S1005.

Allocating a reliability degree as described above enables to lower the reliability degree of a structure erroneously extracted due to the influence of noises. Therefore, the processing according to the present exemplary embodiment is effectively applied to an image that includes a great amount of noise.

Another example method for calculating the reliability degree is described below. When the analysis unit 15 extracts a blood vessel from the eyeground image in step S1004, the analysis unit 15 directly uses a component value obtained for each pixel by the line segment enhancing filter as a reliability degree.

In the present exemplary embodiment, when the structure element is a line segment, the component value is a difference between an average image density value in a structure element and an average value in a local area surrounding the structure element. The component value is calculated for each pixel. A similar value can be calculated using an appropriate differential filter (e.g., the Sobel filter or the Laplacian filter). Therefore, the above-described component value is usable in a case where a differential filter is employed.

Further, as another example, the analysis unit 15 can allocate a higher reliability degree if the same structure is extracted at the same position of the surface image and the projection image, because the possibility of error is low. On the other hand, the analysis unit 15 can allocate a lower reliability degree if an extracted structure is present in only one of the images.

In particular, the extraction accuracy of a blood vessel area or a leucoma from a surface image is generally high. Therefore, the analysis unit 15 can allocate a higher reliability degree if a blood vessel area is extracted solely from a surface image, compared to a reliability degree to be allocated to a blood vessel area extracted solely from a tomography image. As described above, the analysis unit 15 can set an appropriate reliability degree with reference to general characteristics of each image.

In step S1007, the display image generation unit 19 determines structure information to be displayed based on the reliability degree calculated in step S1006. In the present exemplary embodiment, the display image generation unit 19 determines whether to display a blood vessel on a pixel-by-pixel basis with reference to the reliability degree of the blood vessel calculated in step S1006.

Figure 11B:
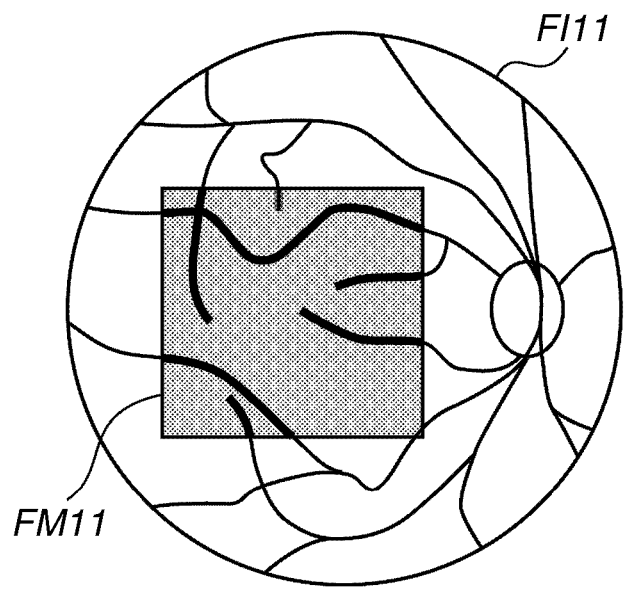
FIG. 11B illustrates another example of the display that can be displayed on the display unit.

As understood from FIG. 11B, the display image generation unit 19 checks the reliability degree of the blood vessel at each pixel of an image FI11 in which the eyeground image and the projection image are overlapped. Then, the display image generation unit 19 adds a reliability degree in the blood vessel extraction result extracted from the eyeground image and a reliability degree obtained from the OCT image.

The display image generation unit 19 displays each pixel as the blood vessel if the summed-up value is equal to or greater than two. An image FM11 includes black bold lines each representing a blood vessel displayed based on the result of the checked reliability degrees.

The image FM11 includes line parts corresponding to the dotted line portions BR111 and BP111 illustrated in FIG. 11A because the reliability degree of each pixel constituting the portions BR111 and BP111 is 3. However, the image FM11 does not include any line part corresponding to the dotted portion BP112 because the reliability degree of each pixel constituting the portion BP112 is 1.

In this manner, if a concerned pixel cannot be easily identified as a blood vessel or noise based on an extraction result solely obtained from the eyeground image or an extraction result solely obtained from the OCT image, the display image generation unit 19 can accurately identify the blood vessel with reference to the reliability degrees obtained from the extraction results of both images.

As another example of the display pattern, the display image generation unit 19 can display a projection image having transparency corresponding to a reliability degree of the extraction. If the reliability degree is high, there is a higher probability that a structure to be checked is present. Therefore, the display image generation unit 19 lowers the transparency to enable a user to easily diagnose the extracted structure.

On the other hand, if the reliability degree is low, there is a lower possibility that a structure to be checked is present. Therefore, the display image generation unit 19 increases the transparency to enable a user to easily check the surface image. The display image generation unit 19 displays an extracted structure with a surrounding frame.

Further, as another example of the display pattern, the display image generation unit 19 can set a transparency according to a difference value between a reliability degree of the extraction obtained from the projection image and a reliability degree of the extraction obtained from the surface image at the same area. If the difference in the reliability degree is a large positive value, the display image generation unit 19 lowers the transparency to enable a user to pay great attention to the projection image.

If the difference in the reliability degree is a large negative value, the display image generation unit 19 increases the transparency to enable a user to pay great attention to the surface image. In this manner, the display image generation unit 19 can set an adequate transparency based on a comparison between the reliability degree obtained from the projection image and the reliability degree obtained from the surface image, and can display a portion to be checked in such a way as to let a user understand easily.

As described above, when the reliability degree is calculated based on a result of extracted structure information, highly reliable information can be provided to each user. Further, when the display pattern is changed according to the reliability degree, users can intuitively understand a portion to be checked from the display. The portion to be checked can be displayed in such a way as to let a user understand easily.

In a fourth exemplary embodiment, the patient data confirmation unit 13 searches for an image of the fundus camera or an SLO image that corresponds to a tomography image in the storage unit 30. If no image can be found in the search, the display image generation unit 19 displays an enlarged projection image as exception processing. Further, the display image generation unit 19 displays the surface image and the tomography image, after they are aligned, in such a way as to rotate the surface image relative to the fixed projection image.

Figure 12:
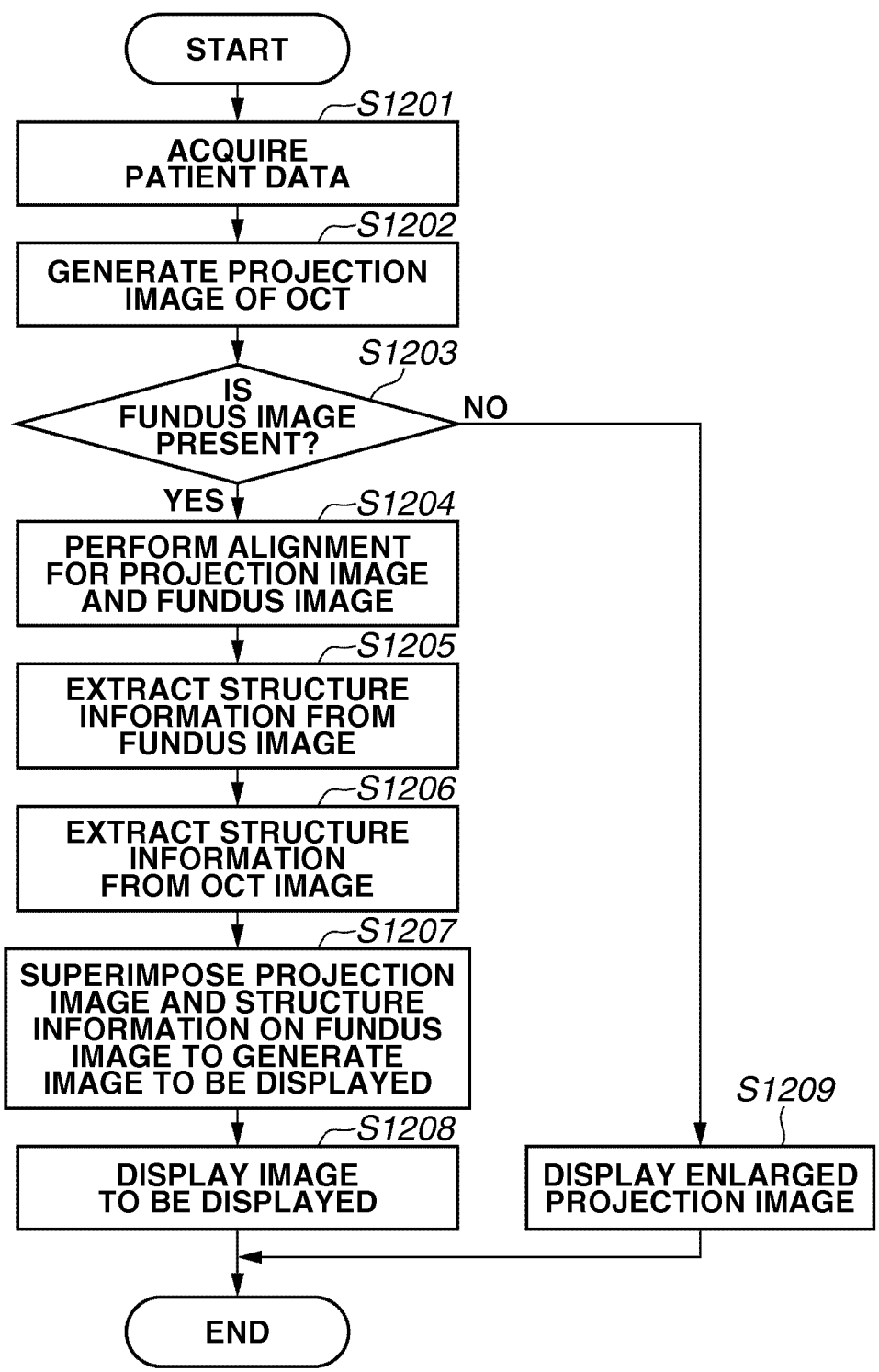
FIG. 12 is a flowchart illustrating an example procedure of another processing that can be performed by the image processing apparatus according to an exemplary embodiment of the present invention.

The present exemplary embodiment is different from the above-described exemplary embodiments in the configuration of the patient data confirmation unit 13 and the display image generation unit 19, as described below. Next, an example flow of processing that can be performed by the image processing apparatus 10 is described below with reference to FIG. 12. Processing to be performed in steps S1201, S1202, and S1204 to S1207 is similar to that described in the first exemplary embodiment and therefore the description thereof is not repeated.

In step S1203, the patient data confirmation unit 13 determines whether both OCT projection image and the eyeground image corresponding each other are stored in the storage unit. the display image generation unit 19 (worked as an image control unit) changes the stored projection image. The patient data confirmation unit 13 checks if there is any eyeground image of the same tested eye that corresponds to the acquired OCT image in the storage unit 30. In the present exemplary embodiment, the patient data confirmation unit 13 determines whether there is any corresponding image captured within a predetermined period of time before the shooting data and time of the tomography image. In another exemplary embodiment, the patient data confirmation unit 13 checks if there is an OCT projection image in the storage unit 30 in response to that an eyeground image is captured or is stored in the storage unit 30. In yet another exemplary embodiment, the patient data confirmation unit 13 checks if both an OCT projection image and a corresponding eyeground image are stored in the storage unit 30. And in still yet another exemplary embodiment, these corresponding images are stored in two or more storage units.

If it is determined that an eyeground image of the same patient is present (YES in step S1203), the processing proceeds to step S1204. If it is determined that there is not any eyeground image of the same patient (NO in step S1203), the processing proceeds to step S1209.

In step S1208, the display image generation unit 19 causes the display unit 40 to display the surface image and the projection image having been aligned. If in step S1204 the alignment unit 14 has acquired an angular component Δθ, the display image generation unit 19 displays the projection image ordinarily. Then, the alignment unit 14 displays the surface image in such a way as to rotate the surface image relative to the already displayed projection image by the angular component Δθ.

Figure 13:
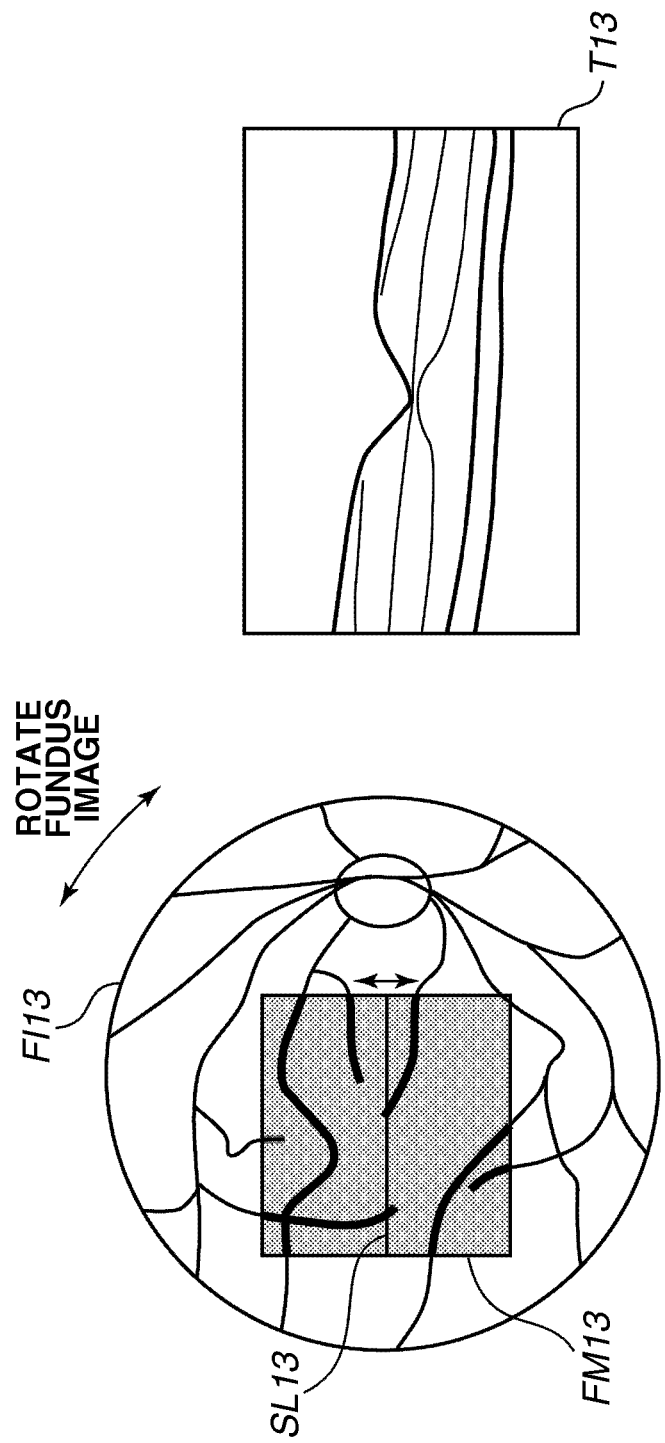
FIG. 13 illustrates another example of the display that can be displayed on the display unit.

FIG. 13 illustrates an example of the display. The example of the display illustrated in FIG. 13 includes a projection image FM13 having a predetermined transparency in a rectangular region surrounded by two sets of line segments respectively parallel to the X direction and the Y direction of the screen. The example of the display illustrated in FIG. 13 further includes an eyeground image FI13 having a nearly circular shape, which has been rotated by the angular component Δθ from the aligned position when displayed.

Further, the example of the display illustrated in FIG. 13 includes a B scanning line SL13 of the OCT superimposed on the projection image. A tomography image T13 corresponding to the scanning line SL13 is displayed together with the surface image. A user can perform a mouse operation to realize a parallel movement of the B scanning line SL13 in the up and down direction.

The display image generation unit 19 displays a corresponding tomography image in response to the positional change of the B scanning line SL13. If the projection image is not rotated when displayed, the B scanning line is kept in parallel to the X direction of the screen on the projection image. Therefore, users can easily perform the mouse operation.

If the projection image displayed on the screen is in a rotated state, the scanning line moves obliquely in accordance with a mouse operation. This is unnatural because the mouse operation performed in the up-and-down direction does not coincide with the moving direction of the line. When the diagnosis is performed while confirming both of the tomography image and the surface image, an intuitive operation easy for each diagnostician can be realized.

In step S1209, the display image generation unit 19 causes the display unit 40 to display the projection image. In this case, the display image generation unit 19 displays an enlarged projection image having a larger size compared to an image to be displayed when the projection image is displayed together with the surface image. The processing in step S1209 is performed based on the intent to display details of the projection image if there is not any surface image to be displayed. Further, the display image generation unit 19 sets the transparency of the projection image to 0 when the projection image is displayed.

In the present exemplary embodiment, it is presumed that at least one tomography image is constantly present. The image processing apparatus 10 determines whether a surface image corresponding to the concerned tomography image is present. However, the system can be configured to search for a tomography image stored in the storage unit 30 in a case where a surface image is already obtained. Further, the system can be configured to check the presence of the other image corresponding to one image.

In a fifth exemplary embodiment, the display image generation unit 19 displays the above-described surface image together with a tomography image indicating the position of a structure extracted from the surface image. An apparatus according to the present exemplary embodiment has a system configuration and performs processing, which are different from those described in the above-described exemplary embodiments. More specifically, the display image generation unit 19 can generate an image different from those described in the above-described exemplary embodiments.

The analysis unit 15 extracts an optic disc portion from the surface image and extracts an optic disc portion from the tomography image. The display image generation unit 19 acquires position coordinates of each optic disc portion extracted by the analysis unit 15. Then, the display image generation unit 19 displays the position of the optic disc portion on the tomography image based on the acquired coordinate values.

Figure 14:
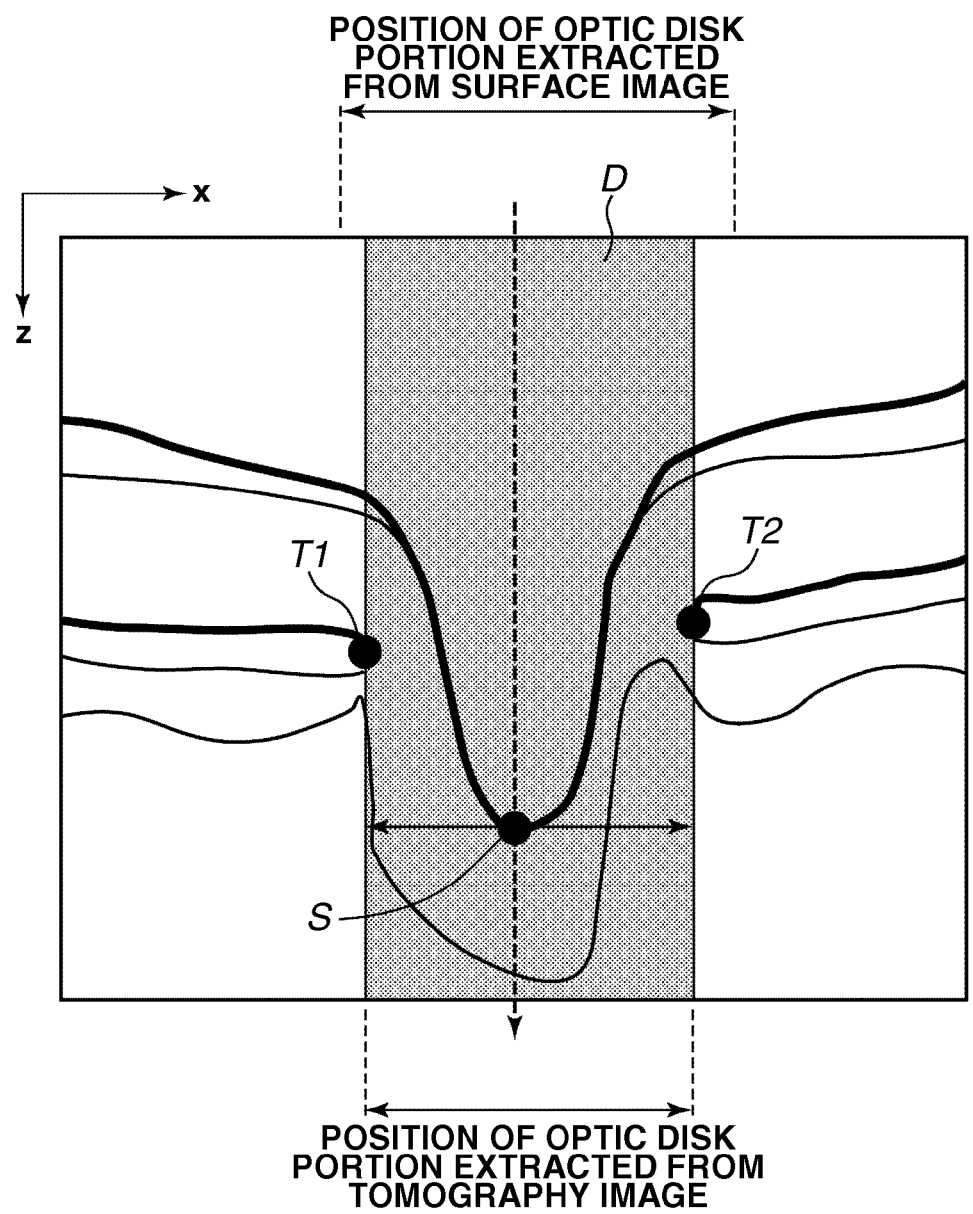
FIG. 14 illustrates another example of the display that can be displayed on the display unit.

FIG. 14 illustrates an example of the display for a tomography image according to the present exemplary embodiment. The display screen includes an indication of the position of an optic disc portion extracted from the surface image, which is displayed along the upper side of the tomography image. Further, the display screen includes an indication of the position of an optic disc portion extracted from the tomography image, which is displayed along the lower side of the tomography image.

As another example, displaying the position of each area (e.g., the "cup" area and the "disc" area) of an optic disc portion on a tomography image using the similar method is feasible. In this case, the displayed screen enables a user to confirm the state of an index of glaucoma (e.g., the "cup" area or the "disc" area) on a tomography image.

As described above, when the position of a structure extracted from a surface image is displayed on a tomography image, users can confirm each structure extracted from both the tomography image and the surface image on the tomography image.

In the above-described exemplary embodiments, the image processing apparatus 10 performs image display processing based on an eyeground surface image captured by the fundus camera and a tomography image captured by the OCT. However, the present invention is not limited to the above-described exemplary embodiments.

For example, the image processing apparatus 10 can simultaneously display an SLO image obtained by the SLO and a tomography image obtained by the OCT or a projection image. Alternatively, the image processing apparatus 10 can simultaneously display a surface image obtained by the fundus camera, an SLO image obtained by the SLO, and a tomography image obtained by the OCT or a projection image.

Further, instead of superimposing a projection image on a surface image, the image processing apparatus 10 can performs display processing in such a way as to directly superimpose a structure extracted from each image on a surface image. Further, the image processing apparatus 10 can display an extracted structure on a schematically illustrated eyeground surface, not on the surface image obtained by the fundus camera. Further, the image processing apparatus 10 can display only the extracted structure.

Further, as another exemplary embodiment, if a structure extracted from a surface image does not coincide with a structure extracted from a tomography image, the image processing apparatus 10 can display a warning (message, graphics, or the like) on the screen to notify a user of the situation. In this case, the apparatus modifies its configuration and processing so that the display image generation unit 19 can display an image accompanied by a warning.

If the extracted blood vessel includes any blood vessel portion extracted solely from a projection image, the display image generation unit 19 can display a text or an image to let a user know such a specific portion. In this case, the user can check the blood vessel portion extracted solely from the tomography image while confirming the displayed text or image.

Further, the display image generation unit 19 can display a specific position where a blood vessel portion extracted from a projection image is discontinuous with a blood vessel portion extracted from a surface image, to let a user know the discontinuity.

Further, as another exemplary embodiment, the display image generation unit 19 can be configured, as a default setting, to cancel the display of any structure extracted solely from a tomography image. In this case, the switching between "display" and "non-display" is controlled according to an instruction input by a user. For example, the display image generation unit 19, which is functionally operable as the display control unit, can be configured to select "display" or "non-display" for each structure extracted solely from the tomography image according to a user's keyboard input.

Further, the display image generation unit 19 can be configured to switch the display pattern for each structure, if it is extracted from both a surface image and a tomography image, according to a user operation. For example, the display image generation unit 19 can add a frame image surrounding the extracted structure.

Further, the display image generation unit 19 can be configured to switch the display pattern for each projection image between "display" and "non-display" according to a user operation. In this case, the user can confirm each image independently or can confirm each image in comparison with the position of a structure extracted by the apparatus. In this manner, the image processing apparatus according to the present exemplary embodiment enables users to confirm the information with a display easy to understand, which is selectable according to user preference.

Further, a plurality of apparatuses can be combined to operate in a decentralized fashion to function cooperatively as an integrated image processing system that can perform the processing executed by the above-described image processing apparatus. The processing to be executed by a single functional block can be realized by a plurality of circuits (or separate functional blocks).

Further, an imaging apparatus or a detector can be modified to incorporate the functions of the image processing apparatus and the display apparatus described in the above-described exemplary embodiments so that the imaging apparatus can realize aspects of the present invention. In this case, for example, the image acquisition unit 11 includes the optical coherence tomography 20. The image acquisition unit 11 causes the optical coherence tomography 20 to capture an image of a target object and acquires a captured image from the optical coherence tomography 20.

The above-described image processing apparatus 10 has an appropriate circuit arrangement that can realize the functions of respective functional blocks. However, employing a mixed software and hardware (computer) arrangement is useful to realize the function corresponding to each block of the image processing apparatus 10.

More specifically, there is an electronic calculator including, for example, a central processing unit (CPU), a read only memory (ROM), a random access memory (RAM), a hard disk drive (HDD), a mouse, a keyboard, a network interface (I/F), and a display device.

For example, a program is stored in the ROM or the HDD. The stored program causes a computer (i.e., the image processing apparatus 10) to realize the functions illustrated in FIG. 1 and execute the processing illustrated in FIG. 4 in cooperation with the hardware of the computer.

Figure 4:
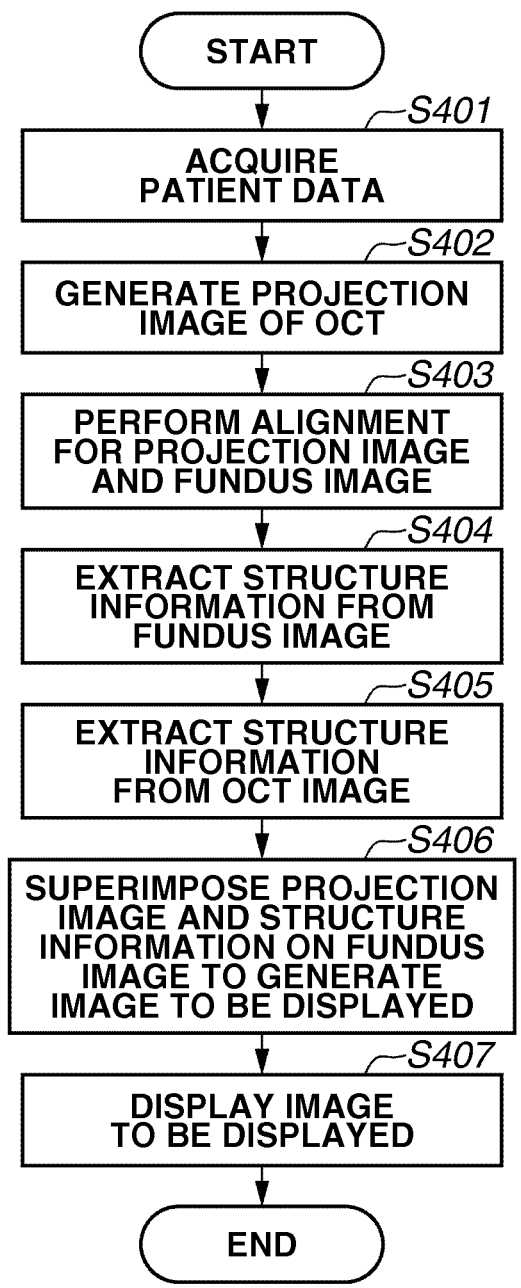
FIG. 4 is a flowchart illustrating an example flow of processing that can be performed by the image processing apparatus according to an exemplary embodiment of the present invention.

The program is loaded into the RAM, and the CPU performs an operation according to instructions of the program to realize the functions illustrated in FIG. 1 and execute the processing illustrated in FIG. 4.

As an exemplary embodiment, a single computer can include a plurality of CPUs. In this case, the plurality of CPUs can perform the above-described processing in a decentralized fashion to realize the functions according to aspects of the present invention.

OTHER EMBODIMENTS

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2010-192385 filed Aug. 30, 2010, which is hereby incorporated by reference herein in its entirety.

What is claimed is:

1. An image processing apparatus comprising:
    an extraction unit configured to extract a structure of a tested eye from an OCT image obtained by optical coherence tomography, and configured to extract a structure of the tested eye from an eyeground image obtained by a scanning laser ophthalmoscope or a fundus camera;
    a calculation unit configured to calculate a reliability degree of the extraction for each of the structure extracted from the OCT image and the structure extracted from the eyeground image based on comparison of the structure extracted from the OCT image and the structure extracted from the eyeground image; and
    a display control unit configured to display each of the structure extracted from the OCT image and the structure extracted from the eyeground image superimposed on the eyeground image in display patterns according to the calculated reliability degree.

2. The image processing apparatus according to claim 1, wherein the display control unit is configured to display the structure extracted from at least one of the OCT image and the eyeground image to have a transparency corresponding to the reliability degree calculated for the extracted structure.

3. The image processing apparatus according to claim 1, wherein
    the calculation unit is configured to calculate a reliability degree of the extraction for each of a plurality of portions with respect to the extracted structure, and
    the display control unit is configured to determine a transparency in the display of the structure extracted from the OCT image in such a way as to set the transparency for a portion having a higher reliability degree to be lower than the transparency for a portion having a lower reliability degree.

4. The image processing apparatus according to claim 1, wherein the display control unit is configured to display an image in such a way as to superimpose a projection image, generated from the OCT image, having a predetermined transparency on the eyeground image, and is configured to display the position of the structure extracted by the extraction unit on the eyeground image.

5. The image processing apparatus according to claim 4, wherein the display control unit is further configured to perform the display in such a way as to discriminate the structure extracted from the OCT image from the structure extracted from the eyeground image.

6. The image processing apparatus according to claim 1, wherein the display control unit is configured to display the position of a structure extracted from the eyeground image by the extraction unit on an OCT tomography image.

7. The image processing apparatus according to claim 1, further comprising:
a determination unit configured to determine whether both the OCT image and the eyeground image corresponding to each other are stored in at least one storage unit,
wherein the display control unit is configured to change the stored image for displaying on the display unit based on the result of the determination.

8. The image processing apparatus according to claim 7, wherein if it is determined that the eyeground image corresponding to a projection image generated from the OCT image is not stored in the storage unit, the display control unit is configured to display the projection image in a size that is larger compared to a size of an image to be displayed when the eyeground image is stored in the memory.

9. The image processing apparatus according to claim 1, further comprising:
an alignment unit configured to acquire an angular component that represents a positional deviation between a projection image generated from the OCT image and the eyeground image,
wherein if the angular component is substantially present, the display control unit is configured to display the eyeground image in such a way as to rotate the eyeground image by the angular component compared to a case where there is substantially not any angular component with respect to the positional deviation.

10. The image processing apparatus according to claim 1, wherein the display control unit further comprises:
an alignment unit configured to align positional deviation between a projection image generated from the OCT image and the eyeground image; and
a notification unit configured to notify of a position where the position of a blood vessel extracted from the OCT image by the extraction unit is discontinuous with the position of a blood vessel extracted from the eyeground image, based on a result of the alignment by the alignment unit.

11. The image processing apparatus according to claim 1, wherein the extraction unit is configured to extract at least one of a blood vessel, an optic disc portion, a macula portion, and a leucoma from a OCT tomography image and is configured to extract at least one of a blood vessel, an optic disc portion, a macula portion, a leucoma and a choroidal neovascularization from the eyeground image.

12. An image processing system comprising:
the image processing apparatus defined in claim 1; and
a display unit configured to display the eyeground image in such a way as to display a position of the structure extracted by the extraction unit on the eyeground image.

13. An image processing method comprising:
extracting a structure of a tested eye from an OCT image obtained by an optical coherence tomography;
extracting a structure of the tested eye from an eyeground image obtained by a scanning laser ophthalmoscope or a fundus camera;
calculating a reliability degree of the extraction for each of the structure extracted from the OCT image and the structure extracted from the eyeground image based on comparison of the structure extracted from the OCT image and the structure extracted from the eyeground image;
superimposing each of the structure extracted from the OCT image and the structure extracted from the eyeground image on the eyeground image in display patterns according to the calculated reliability degree; and
displaying the superimposed eyeground image.

14. A non-transitory computer readable memory storing a program that causes a computer to execute:
processing for extracting a structure of a tested eye from an OCT image obtained by an optical coherence tomography;
processing for extracting a structure of the tested eye from an eyeground image obtained by a scanning laser ophthalmoscope or a fundus camera;
processing for calculating a reliability degree of the extraction for each of the structure extracted from the OCT image and the structure extracted from the eyeground image based on comparison of the structure extracted from the OCT image and the structure extracted from the eyeground image; and
processing for generating an image in such a way as to superimpose each of the structure extracted from the OCT image and the structure extracted from the eyeground image on the eyeground image in display patterns according to the calculated reliability degree.

* * * * *